United States Patent [19]
Schmidt

[11] Patent Number: 5,011,587
[45] Date of Patent: Apr. 30, 1991

[54] APPARATUS FOR THE DETECTION OF CHEMICAL EQUALIZATION PROCESSES IN AN AQUEOUS SOLUTION

[75] Inventor: Wilhelm Schmidt, Lörrach, Fed. Rep. of Germany

[73] Assignee: Ciba-Geigy Corporation, Ardsley, N.Y.

[21] Appl. No.: 484,715

[22] Filed: Feb. 26, 1990

[30] Foreign Application Priority Data

Mar. 2, 1989 [CH] Switzerland .......................... 775/89

[51] Int. Cl.$^5$ ............................................. G01N 27/28
[52] U.S. Cl. ................................. 204/401; 204/409; 204/433
[58] Field of Search ............... 204/401, 409, 410, 411, 204/433

[56] References Cited

U.S. PATENT DOCUMENTS 2,884,365  4/1959  Bolt et al. ........................ 204/433 X
4,202,749  5/1980  Phelps et al. ........................ 204/409

FOREIGN PATENT DOCUMENTS 0271764  9/1988  European Pat. Off. .
3118771  11/1982  Fed. Rep. of Germany .
3525401  12/1986  Fed. Rep. of Germany .
8706309  9/1988  Fed. Rep. of Germany .

OTHER PUBLICATIONS

Ingold Prospectus-InTrac 776.

Primary Examiner—G. L. Kaplan
Attorney, Agent, or Firm—Harry Falber

[57] ABSTRACT

An apparatus for the detection of chemical equalization processes in aqueous solutions, in particular for the determination of pH values and/or redox potentials, is described. The apparatus, a so-called interchangeable probe, includes an essentially cylindrical probe body, with a calibrating chamber and with an immersion pipe axially displaceable in a bore of the probe body and having at its front end a protective cylinder, the area adjacent to the immersion pipe being perforated in a basket-like manner. An electrode is set into the immersion pipe with the head of the electrode being located within the basket like perforated area of the protective cylinder. An annular gap between the immersion pipe and the inner wall of the probe body is sealed by at least three gaskets, located on the inner wall of the probe body. The first gasket is located above the calibrating chamber and the second and the third gaskets are located under the calibrating chamber and the distance between two adjacent gaskets is larger than the length of the perforated area.

12 Claims, 3 Drawing Sheets

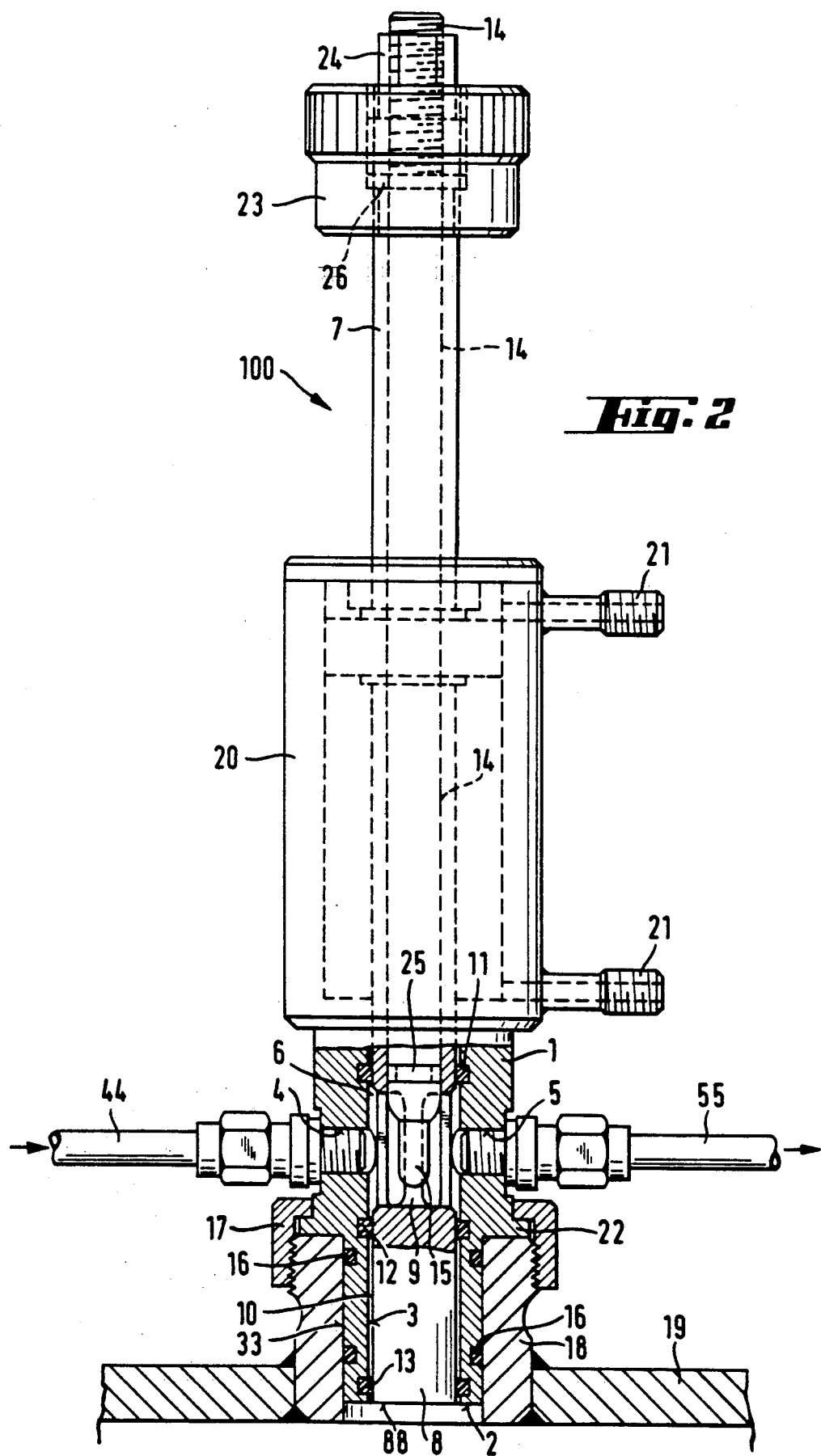

APPARATUS FOR THE DETECTION OF CHEMICAL EQUALIZATION PROCESSES IN AN AQUEOUS SOLUTION

BACKGROUND OF THE INVENTION

The present invention relates to an apparatus for the detection of chemical equalization processes in aqueous solutions, in particular for the determination of pH values and/or redox potentials, with an essentially cylindrical probe body, provided with at least one inlet and one outlet opening for calibrating or flushing liquids, which open into a calibrating chamber in the forward area of the probe body, and an immersion pipe axially displaceable in a bore of the probe body and including a protective cylinder at its front end into which an electrode is set, with the head of said electrode being located within a basket like perforated area of the protective cylinder.

Numerous chemical reactions take place in an aqueous solution. In particular in industrial chemistry it is of enormous economical and ecological importance to be able to detect reaction processes, which usually are equilibrium processes, by means of measuring techniques. For this purpose, the pH value and/or the redox potential are conventionally determined in aqueous solutions. Thus, for example, the accurate detection of end points by means of pH and or redox potential determination in the diazotization of amines makes possible titration in the initial operating mixture. This yields information concerning the input quantities of the reagents effectively required. By the resulting nitrite addition optimized relative to minimum requirements it is possible to largely avoid the generation of nitrous gases and thus of $NO_x$ emissions. PH values and redox potentials of solutions in industrial chemistry are usually determined by means of pH or redox probes, inserted through openings provided in the reaction vessel. In a known apparatus a rubber coated steel probe is inserted into the reaction vessel; it is capable of carrying up to three measuring electrodes on its tip. Steel probes of this type are very cumbersome and heavy. For the replacement and the calibration of the electrodes it must be raised by a winch from the vessel, following the release of a screw fastening. Other, lighter steel probes carry one electrode only, but are simpler and may be installed and removed more rapidly. However, for replacement and electrode calibration, they must also be screwed out of the vessel. Furthermore, the light configuration gives rise to stability problems in the case of greater lengths.

The German utility patent DE-U-87 06 309 describes a measuring probe permanently protruding into the reaction vessel. The calibrating chamber may be closed only by means of an additional closure cover relative to the vessel. If the closure mechanism is defective, no calibration of the electrode is possible and the safe replacement of the electrode is not assured. DE-A-3 525 401 describes a probe making it possible to insert and remove the electrode into and from the reaction vessel. However, in order to safely replace the electrode, additional closure elements (valves) must be actuated, which creates an additional safety risk.

The probes described in DE-A-3,118,771 and EP-A-271,764 permanently protrude into the reaction vessel. In order to calibrate or to wash the electrode a sleeve member is slipped onto the electrode, thus creating a calibration chamber. Additional valves are necessary to separate the calibration chamber from the surroundings. The sleeve member cannot be fully drawn into the body of the probe, so that a dead space is present, in which residues may be deposited. This represents an enormous safety risk especially in the case of diazotizing reactions which often involve explosive residues.

A significant improvement relative to the known rod probes is provided, for example, by the interchangeable probes described in the prospectuses No. 776-2-D-300.087 CB and No. 777-1-D of the Ingold Messtechnik GmbH Co., Siemensstrasse 9, D-6347 Steinbach/TS. These interchangeable probes are substantially smaller than the rod probes described above and are mounted laterally over the bottom of the reaction vessel. An immersion pipe with the electrode may be inserted into and removed from the vessel, even during production runs. This provides the preconditions for automatic electrode calibration and automatic reaction control. To replace the electrode, it is simply removed from the immersion pipe and another inserted. If the immersion pipe is withdrawn from the reaction vessel, the opening in the immersion pipe toward the reaction vessel is closed by a protective cylinder provided on the tip of the probe. However, these probes are not always tight in all of the positions of the immersion pipe. Particularly during the passage of the immersion pipe through its intermediate position, liquid from the vessel may briefly be ejected into nonsealing areas of the probe, for example into the calibrating chamber or flushing lines. In particular, in case of a failure of control air, the pneumatically operated immersion pipe may occupy an undefinable position between its terminal inserted and retracted positions and the vessel liquid, which frequently is under pressure, may escape out of control. In diazotizing reactions, special care must be taken to avoid deposits in dead spaces of the probe, as said deposits are often explosive.

It is therefore an object of the present invention to improve an interchangeable electrode of the above described type so that the problems cited are eliminated.

SUMMARY OF THE INVENTION

This object is attained according to the invention by modifying the existing interchangeable probe to include an annular gap between the immersion pipe and the inner wall of the probe body which is sealed by at least three spaced apart gaskets located on the inner wall of the probe body, a distance between two adjacent gaskets being larger than the length of the perforated area of the protective cylinder, and a first gasket being located above the calibrating chamber and a second and third gasket being located under the calibrating chamber. Preferred variants are the object of dependent claims.

BRIEF DESCRIPTION OF THE DRAWINGS

Other objects and advantages will become apparent from the following detailed description of a preferred embodiment of the invention as described in conjunction with the accompanying drawings wherein like reference numerals are applied to like elements and wherein:

FIG. 2 shows an interchangeable probe with the immersion pipe inserted, in a partial section.

DETAILED DESCRIPTION OF THE PREFERRED EMBODIMENTS

Figure 1:
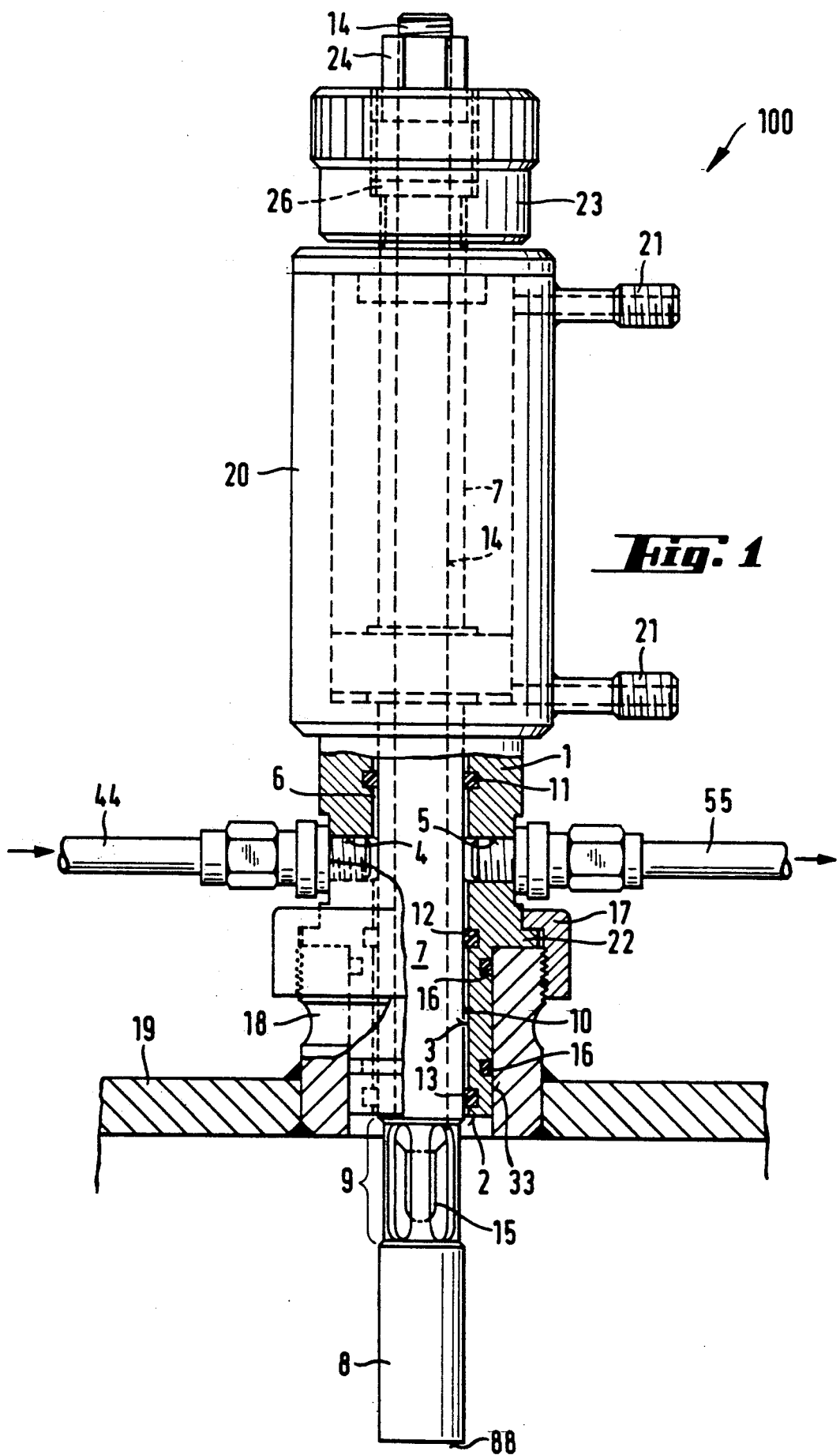
FIG. 1 shows an interchangeable probe with its immersion pipe retracted, in a partial section.
Figure 3:
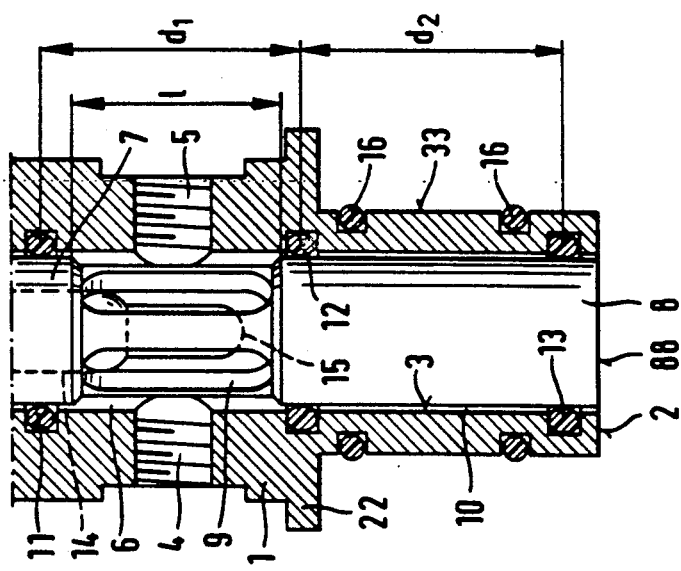

The interchangeable probe shown in FIGS. 1 and 2 and designated 100 in its entirety, corresponds in its fundamental configuration to the probe described in the aforecited prospect No. 777-1-D of the Ingold Co. The following description is therefore restricted to details essential for the invention. The interchangeable probe 100 comprises an essentially cylindrical probe body 1 with a centered axial bore. The probe body 1 is equipped with at least one inlet and outlet opening 4 and 5, opening into the calibrating chamber 6 in the forward area of the probe body 1. Inlet and outlet lines 44 and 55 may be connected with or screwed into the inlet and outlet openings 4 and 5. Calibrating or flushing liquids may be introduced into or removed from the calibrating chamber 6 by means of said inlet and outlet lines 44 and 55. An immersion pipe 7 is located in the bore of the probe body 1 in an axially displaceable manner. The diameter of the immersion pipe 7 is slightly smaller than the diameter of the bore of the probe body 1, so that between the inner wall 3 of the probe body 1 and the immersion pipe 7 an annular gap 10 is provided, in order to assure the ready displacement of the immersion pipe 7. Above and below the calibrating chamber 6 the annular gap 10 is sealed against the liquid by a first and second gasket in the form of an O ring 11 and 12. The first and second O ring 11 and 12 are let into the inner wall 3 of the probe body 1 spaced apart at a distance $d_1$ (FIG. 3). The outer wall of the probe body 1 is provided approximately at the height of the first O ring 11 with an annular bead 22, which supports a union nut 17. The probe body 1 may be screwed by means of said union nut 17 onto the standardized opening fitting 18 of the chemical reactor vessel 19, so that its forward portion is projecting into the fitting 18. O rings 16 are let into the outer wall 33 of the forward area of the probe body 1 as a seal against the liquid in the vessel.

The interchangeable probe 100 is preferably screwed onto the opening fitting 18 or lateral loose flanges in the bottom area of the reactor vessel 19. Such interchangeable probes (100) may also be screwed onto the opening fittings of pipelines, so that the immersion pipe may be inserted into the pipeline.

The immersion pipe 7 is equipped at its forward end with a protective cylinder 8. The area 9 of the protective cylinder 8 directly connected with the front end of the immersion pipe 7 is perforated in the form of a basket. A head part 15 of an electrode 14 located in the immersion tube 7 is positioned exactly inside the perforated basket like area 9 of the protective cylinder 8. The immersion tube 7 is sealed against the liquid of the vessel by an O ring, not shown, behind the head part 15 of the electrode 14. The rear end of the immersion pipe 7 may be closed off by a screw part 23. The screw part 23 is provided with an opening for the electrode 14 and supports a fastening nut 24 for the electrode 14. By simply loosening the fastening nut 24, different electrodes 14 may be introduced into the immersion pipe 7 for pH or redox potential or other, for example ion sensitive, measurements. An O ring, not shown is adhesively bonded to the outer wall of the electrode 14, so that it may be clamped between the rear end of the immersion pipe 7 and the fastening nut 24. In this manner the immersion pipe 7 is sealed against the environment and the electrode 14 is prevented from dropping into the vessel 19 in case of a fracture.

The probe body 1 is preferably mounted within a pneumatic cylinder 20. In this case the immersion pipe 7, shown in FIGS. 1 and 2 in its two terminal positions—extended for measurement in FIG. 1 and withdrawn in FIG. 2—is also the pneumatic piston. Compressed air is passed into the pneumatic cylinder through control air connections 21 and is used to displace the immersion pipe 7.

Figure 5:
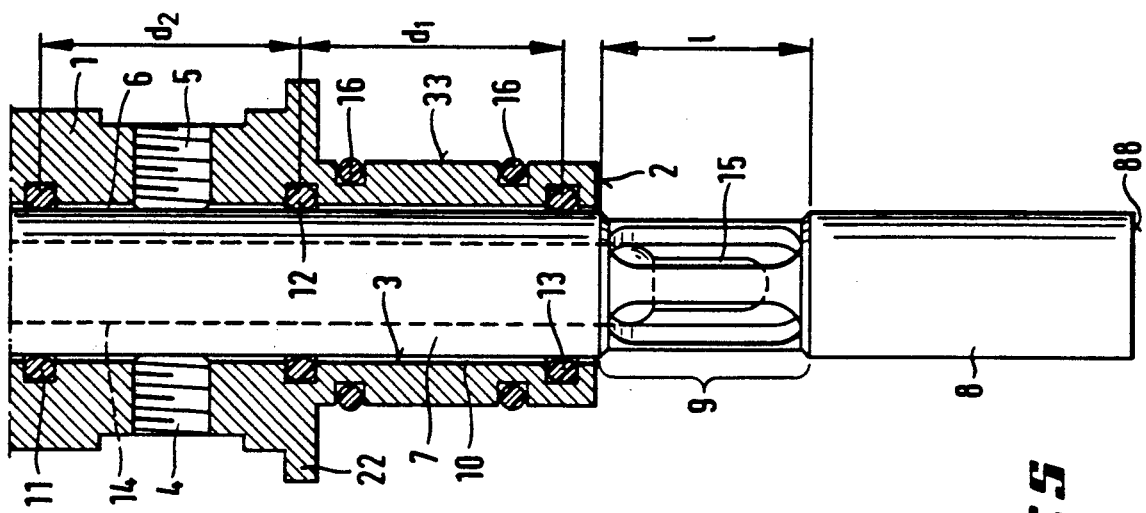
FIGS. 3-5 show a partially sectioned and enlarged detailed view of the interchangeable probe with three positions of the immersion pipe.
Figure 4:
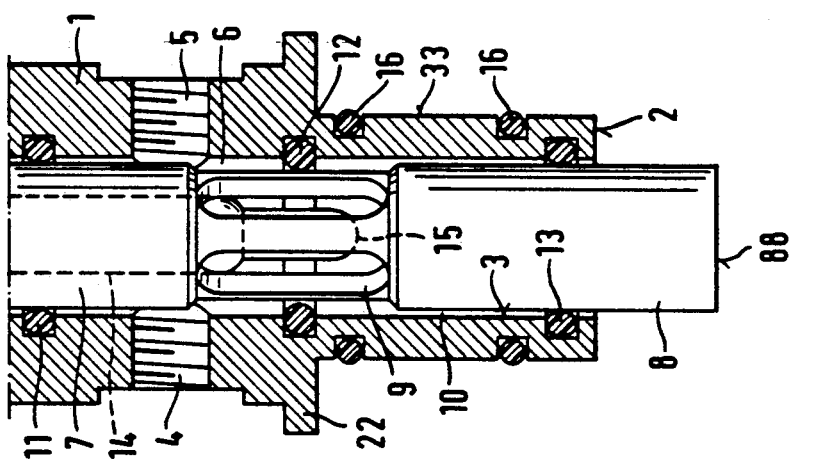

In FIGS. 3-5 the part of the interchangeable probe 100 essential for the invention is shown enlarged. For the sake of clarity, in FIGS. 3-5 the union nut 17 and the outer O rings 16 are eliminated. In FIG. 3 the immersion pipe 7 is shown in its retracted terminal position, in FIG. 4 in an intermediate position and in FIG. 5 in its extended terminal position. In FIGS. 3-5, in the foremost area of the probe body 1, a third gasket is shown in the form of the O ring 13, let into the inner wall 3 and spaced apart at a distance $d_2$ from the second O ring 12. The front, unperforated part of the protective cylinder 8 is extended, so that it abuts in the retracted terminal position of the immersion pipe 7 both against the second and the third O ring 12 and 13, thus being longer than the distance $d_2$ between the second and the third O ring 12 and 13. The basket like, perforated area 9 of the protective cylinder 8, on the other hand, has a length 1, which is smaller than the distances $d_1$ and $d_2$ between the first O ring 11 and the second O ring 12, and between the second O ring 12 and the third O ring 13. It is assured in this manner that even in the intermediate positions (FIG. 4) of the immersion pipe 7, during the transition from one terminal position to the other, at least one O ring always seals off the annular gap 10 between the inner wall 3 of the probe body 1 and the immersion pipe 7. In a particularly preferred embodiment, a circumferential lip seal is let into the inner wall 3 of the probe body 1, in addition to the third O ring 13. This additional lip seal may be located in front or behind the third O ring 13. As an alternative, in place of the third O ring 13 and the lip seal, a double lip seal gasket may be provided in the inner wall 3 of the probe body 1, or the foremost third gasket may be in the form of a packing box.

In a preferred manner the distances $d_1$ and $d_2$ are of equal length. The length of the protective cylinder is preferably such that in the retracted terminal position of the immersion pipe 7 the front end 88 of the protective cylinder 8 is flush with the front end of the probe body 1. It is assured in this manner that no vessel liquid can accumulate in the dead spaces of the interchangeable probe 100.

In the extended terminal position (FIG. 5), the basket like perforated area 9 of the protective cylinder 8 protrudes past the front end of the probe body 1 and into the liquid in the vessel. In the retracted terminal position of the immersion pipe 7 (FIG. 3) the perforated area 9 is inside the calibrating chamber 6, wherein for example residues of the vessel liquid may be flushed off the electrode head 15.

The preferred material for the calibrating chamber 6, the immersion pipe 7 and the protective basket 8 is Hastelloy C4. The O rings are preferably made of Kalrez ®. The electrodes 14 and the electrode head 15 consist of glass. Electrodes of the Ingold Co. are used preferably in particular Xerolyt ® electrodes, described in the company prospect No. XER-1-D. Other electrodes use as the reference medium electrolyte pastes under pressure. Still others have configurations such that the reference medium may be exchanged or refilled.

The configuration according to the invention of the interchangeable probe 100 assures that no vessel liquid can escape in any position of the immersion pipe 7 if the liquid in the vessel is under pressure and if there is a failure of the control air in pneumatically operated probes 100. By a suitable choice of the length of the cylinder 8, the accumulation of liquid residues in the dead spaces of the probe is prevented, whereby the safety of the apparatus is further enhanced.

It will be appreciated by those of ordinary skill in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. Apparatus for the detection of chemical equalization processes in aqueous solutions comprising an essentially cylindrical probe body, provided with at least one inlet and one outlet opening for calibrating or flushing liquids, which open into a calibrating chamber in the forward area of the probe body;

an immersion pipe axially displaceable in a bore of the probe body and including a protective cylinder with a front end into which an electrode is set, with the head of said electrode being located within a basket-like perforated area of the protective cylinder; and, an annular gap between the immersion pipe and the inner wall of the probe body which is sealed by at least three spaced apart gaskets located on the inner wall of the probe body, a distance between two adjacent gaskets being larger than the length of the perforated area of the protective cylinder, and a first gasket being located above the calibrating chamber and a second and third gasket being located under the calibrating chamber.

2. Apparatus according to claim 1, wherein the immersion pipe may be immobilized in two terminal positions, the perforated area of the protective cylinder being projected in an extended terminal position past the front end of the prove body and being located in a retracted terminal position within the calibrating chamber.

3. Apparatus according to claim 2, wherein a front end of the protective cylinder in the retracted terminal position of the immersion pipe is flush with the front end of the probe body.

4. Apparatus according to claim 1, wherein the distance between the first gasket and the second gasket and the distance between the second gasket and the third gasket are equal in length.

5. Apparatus according to claim 1, wherein the electrode and the electrode head are made of glass and the electrode is filled with a reference medium.

6. Apparatus according to claim 5, wherein the reference medium is an electrolyte.

7. Apparatus according to claim 5, wherein the reference medium consists of an electrolyte paste.

8. Apparatus according to claim 7, wherein the electrode has means to permit the addition and withdrawal of the reference medium.

9. Apparatus according to claim 5, wherein the electrode has means to permit the addition and withdrawal of the reference medium.

10. Apparatus according to claim 1, wherein the probe body additionally contains a pneumatic cylinder and said immersion pipe is the pneumatic piston thereof.

11. Apparatus according to claim 1, wherein the probe body contains screw means to permit its attachment to an opening of a chemical reactor vessel or a pipeline, so that the immersion pipe may be inserted into the vessel or the pipeline.

12. Apparatus according to claim 1, wherein the gaskets are in the form of O rings.

* * * * *